US012642445B2

(12) United States Patent
Kobayashi et al.

(10) Patent No.: US 12,642,445 B2
(45) Date of Patent: Jun. 2, 2026

(54) BLOOD PRESSURE MEASUREMENT SYSTEM

(71) Applicant: OMRON HEALTHCARE CO., LTD., Muko (JP)

(72) Inventors: Yuka Kobayashi, Kyoto (JP); Shingo Yamashita, Kyoto (JP); Masaki Yamada, Kyoto (JP)

(73) Assignee: OMRON HEALTHCARE CO., LTD., Muko (JP)

( * ) Notice: Subject to any disclaimer, the term of this patent is extended or adjusted under 35 U.S.C. 154(b) by 1053 days.

(21) Appl. No.: 17/745,394

(22) Filed: May 16, 2022

(65) Prior Publication Data

US 2022/0273178 A1      Sep. 1, 2022

Related U.S. Application Data

(63) Continuation of application No. PCT/JP2020/042300, filed on Nov. 12, 2020.

(30) Foreign Application Priority Data

Nov. 26, 2019      (JP) ................................. 2019-213174

(51) Int. Cl.
*A61B 5/022*      (2006.01)
*A61B 5/00*      (2006.01)
(52) U.S. Cl.
CPC ................ *A61B 5/022* (2013.01); *A61B 5/74* (2013.01)
(58) Field of Classification Search
CPC ......... A61B 5/022; A61B 5/74; A61B 5/4806; A61B 5/6824; A61B 5/6898
See application file for complete search history.

(56) References Cited

U.S. PATENT DOCUMENTS

2010/0180207 A1 * 7/2010 MacGuire .......... G06Q 30/0603
715/745
2011/0076994 A1 * 3/2011 Kim ..................... G06Q 10/109
455/414.2
(Continued)

FOREIGN PATENT DOCUMENTS

CN      108766423 A  * 11/2018  ............. G10L 15/22
CN      109922714 A      6/2019
(Continued)

OTHER PUBLICATIONS

English-language machine translation of CN 108766423 A (Year: 2025).*

(Continued)

*Primary Examiner* — Andrey Shostak
(74) *Attorney, Agent, or Firm* — OLIFF PLC

(57)      ABSTRACT

A blood pressure measurement system includes a sphygmomanometer having a nighttime blood pressure measurement mode for automatically starting blood pressure measurement according to a predetermined schedule, and an information terminal capable of communicating with the sphygmomanometer. The sphygmomanometer includes a mode operation unit that sets the sphygmomanometer to the nighttime blood pressure measurement mode. At least one of the sphygmomanometer and the information terminal includes a storage unit that stores measurement time at which blood pressure measurement was performed in the nighttime blood pressure measurement mode. The information terminal includes reminding time calculation unit that calculates reminding time for notifying the subject that the sphygmomanometer should be set to nighttime blood pressure measurement mode based on the measurement time stored in the storage unit, and a notification unit that notifies the subject of that the sphygmomanometer should be set to the night- (Continued)

time blood pressure measurement mode at the reminding time.

8 Claims, 8 Drawing Sheets

(56) References Cited

U.S. PATENT DOCUMENTS

2018/0315294 A1* 11/2018 Takano ................ G08B 25/001
2019/0380624 A1* 12/2019 Ota ........................ A61B 5/1116

FOREIGN PATENT DOCUMENTS

| | | |
|---|---|---|
| CN | 110381822 A | 10/2019 |
| JP | 2001-070260 A | 3/2001 |
| JP | 2006-198030 A | 8/2006 |
| JP | 2013-183974 A | 9/2013 |
| JP | 2016-140641 A | 8/2016 |
| JP | 2018-149173 A | 9/2018 |
| WO | WO-2018168797 A1 * | 9/2018 ............. A61B 5/021 |

OTHER PUBLICATIONS

Sep. 11, 2024 Office Action issued in Chinese Patent Application No. 202080081192.7.
Jan. 12, 2021 International Search Report issued in International Patent Application No. PCT/JP2020/042300.

* cited by examiner

BLOOD PRESSURE MEASUREMENT SYSTEM

CROSS-REFERENCE TO RELATED APPLICATIONS

This is a continuation application of International Application No. PCT/JP2020/042300, with an International filing date of Nov. 12, 2020, which claims priority of Japanese Patent Application No. 2019-213174 filed on Nov. 26, 2019, the entire content of which is hereby incorporated by reference.

TECHNICAL FIELD

The present invention relates to a blood pressure measurement system, and more particularly to a blood pressure measurement system including a sphygmomanometer having a nighttime (sleep) blood pressure measurement mode.

BACKGROUND ART

Patent Document 1 (JP 2006-198030 A) discloses a technique in which a time at which blood pressure measurement should be performed is set in advance, and when the time comes, a subject is notified of the time by display, vibration, sound, or the like. This can prevent the subject from forgetting the blood pressure measurement.

SUMMARY OF THE INVENTION

The present applicant has previously proposed a sphygmomanometer that performs blood pressure measurement at night, the sphygmomanometer having a mode (referred to as "nighttime blood pressure measurement mode") for automatically starting blood pressure measurement according to a predetermined schedule (for example, Japanese Patent Application Laid-Open No. 2019-149007 and Japanese Patent Application Laid-Open No. 2019-195246). When this sphygmomanometer once enters the nighttime blood pressure measurement mode, a subject does not forget to measure the blood pressure.

In contrast, this sphygmomanometer is scheduled to enter the nighttime blood pressure measurement mode by operation by the subject when the subject goes to bed. For this reason, if the subject forgets to perform the operation, a situation where the blood pressure measurement at night is not performed at all may occur. Here, a time when the subject goes to bed may be different every day depending on various lifestyle of the subject, and thus, is not specified at a certain time. For this reason, the technique for notifying the subject that a certain time has come as disclosed in Patent Document 1 is insufficient.

The present invention has been made to solve the above-described problem, and an object of the present invention is to provide a blood pressure measurement system that includes a sphygmomanometer having a nighttime blood pressure measurement mode and can notify a subject that the sphygmomanometer should be set to the nighttime blood pressure measurement mode.

In order to achieve the object, a blood pressure measurement system of the present disclosure comprises a sphygmomanometer having a nighttime blood pressure measurement mode for automatically starting blood pressure measurement according to a predetermined schedule; and an information terminal communicable with the sphygmomanometer, wherein the sphygmomanometer includes a mode operation unit that inputs an instruction to set the sphygmomanometer to the nighttime blood pressure measurement mode, at least one of the sphygmomanometer and the information terminal includes:

a storage unit that stores measurement times at which blood pressure measurement was performed in the nighttime blood pressure measurement mode; and a reminding time calculation unit that calculates a reminding time at which a subject is notified of that the sphygmomanometer should be set to the nighttime blood pressure measurement mode based on the measurement times stored in the storage unit, and the information terminal includes a notification unit that notifies the subject that the sphygmomanometer should be set to the nighttime blood pressure measurement mode at the reminding time.

In the present description, the sphygmomanometer and the information terminal can typically communicate with each other in a state of being separated from each other.

Further, the "mode operation unit" may be, for example, a switch provided in a main body of the sphygmomanometer, and may receive switching on by the user as an instruction, or may be composed of a communication unit that receives an instruction from a smartphone or the like existing outside the sphygmomanometer via wireless communication.

Depending on a schedule, a next "reminding time" may be set in a time zone several hours before the "measurement time" at which the blood pressure measurement was performed. Here, the "measurement time" and the "reminding time" do not include a date and define only a time.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

MODE(S) FOR CARRYING OUT THE INVENTION

Hereinafter, an embodiment of a blood pressure measurement system according to the present invention will be described with reference to the accompanying drawings.

[Blood Pressure Measurement System]

Figure 1:
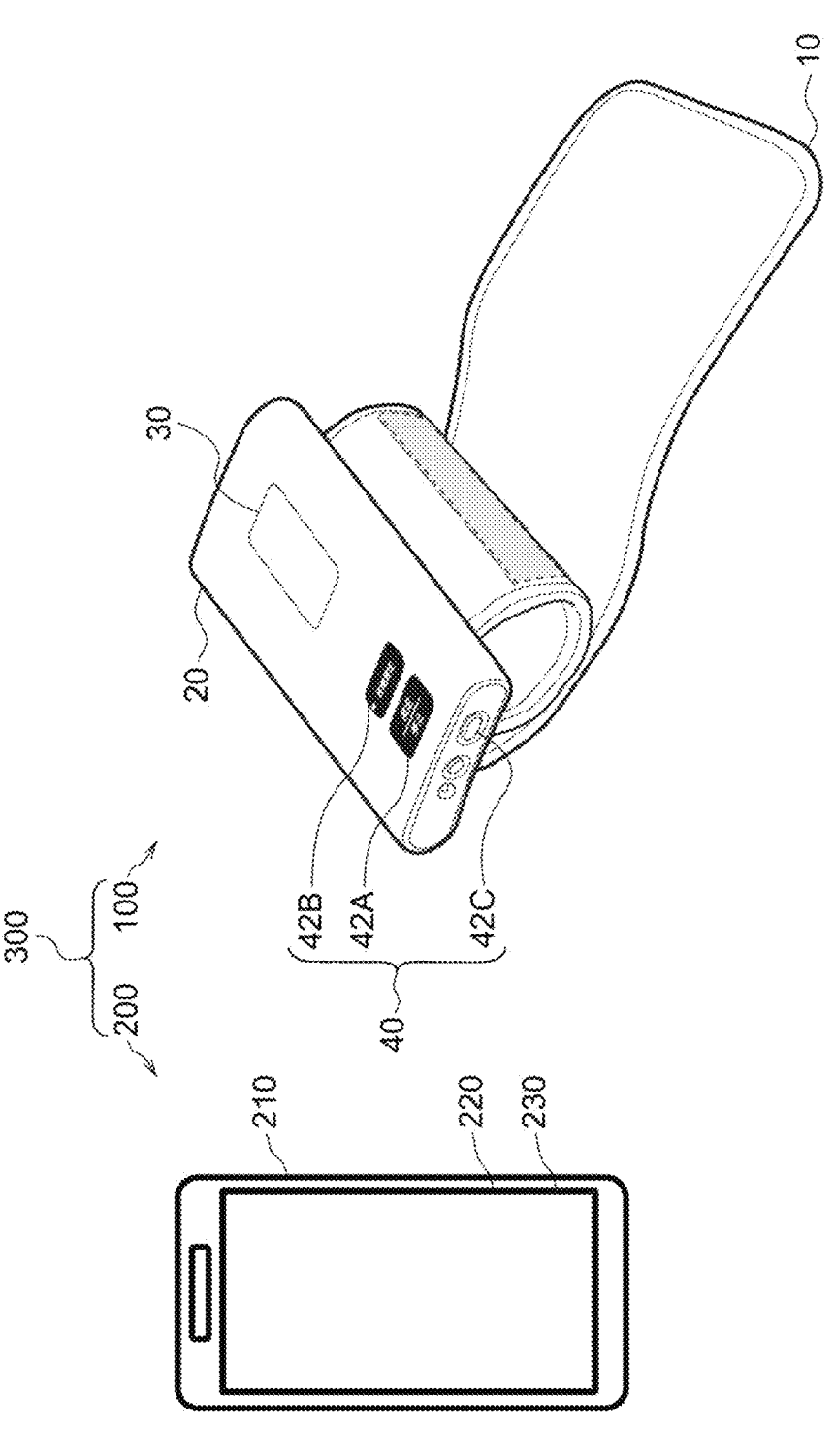
FIG. 1 is a schematic diagram of a blood pressure measurement system including a wrist-type sphygmomanometer and a smartphone according to an embodiment of the present invention.

FIG. 1 illustrates a schematic configuration of a blood pressure measurement system 300 according to an embodiment of the present invention. The blood pressure measurement system 300 includes a wrist-type sphygmomanometer (hereinafter, appropriately referred to as the "sphygmomanometer") 100 and a smartphone (information terminal) 200. As will be described later, the sphygmomanometer 100 has a normal blood pressure measurement mode in which blood pressure measurement is started immediately after a blood pressure measurement switch is turned on, and a nighttime blood pressure measurement mode in which blood pressure measurement is started according to a predetermined schedule. Further, the sphygmomanometer 100 and the smartphone 200 are provided to be separated from each other, and are communicable with each other by Bluetooth® low energy (BLE; low power consumption Bluetooth®) communication.

[Configuration of Sphygmomanometer]

As illustrated in FIG. 1, the sphygmomanometer 100 includes a cuff 10 for blood pressure measurement wound around a measurement target site of a subject and a sphygmomanometer main body 20 integrally attached to the cuff 10.

Figure 2:
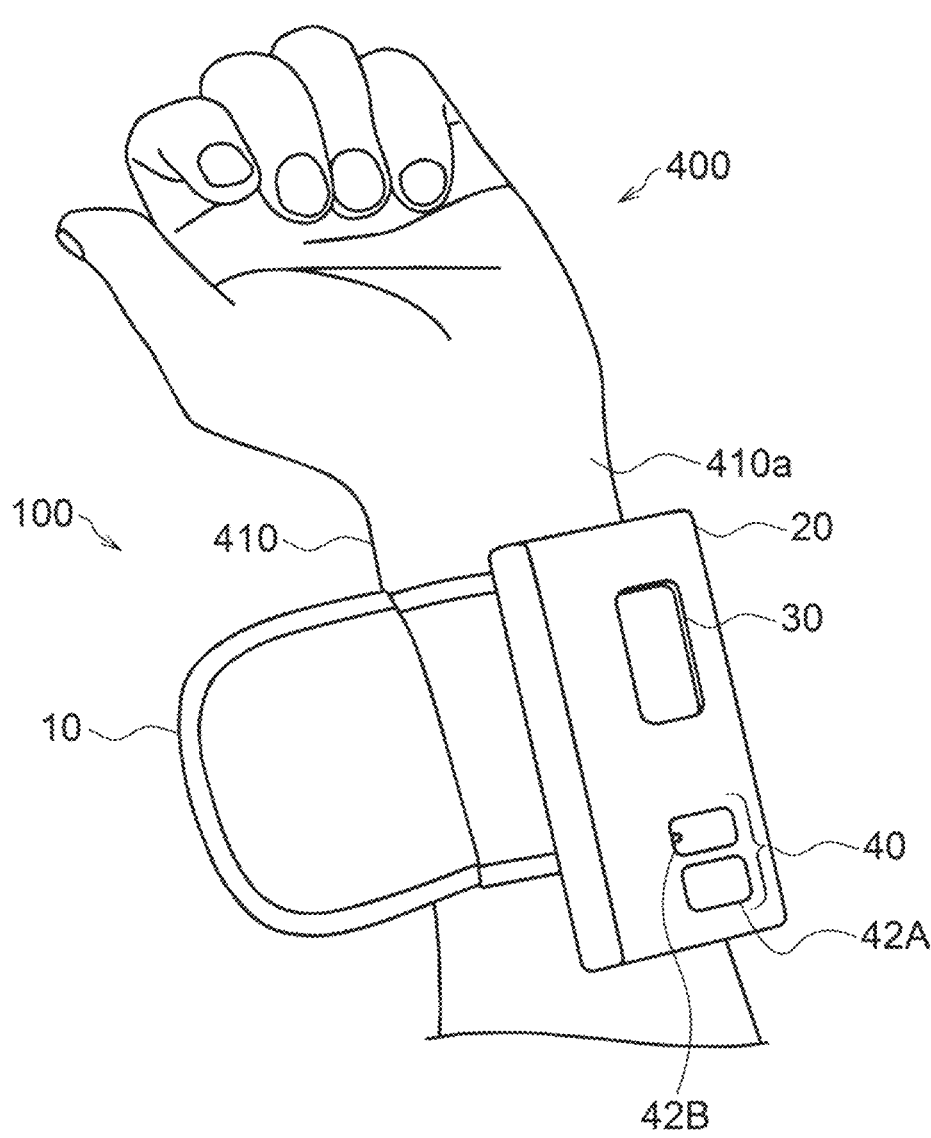
FIG. 2 is a schematic view illustrating a state in which the wrist-type sphygmomanometer illustrated in FIG. 1 is wound around a left wrist.

As illustrated in FIG. 2, the sphygmomanometer 100 according to the embodiment is a wrist-type sphygmomanometer. Therefore, the cuff 10 has an elongated band-like shape so as to be wound around a left wrist 410 of a subject 400, for example. The cuff 10 contains an air bag 12 (see FIG. 3) for compressing the left wrist 410. Note that, in order to always maintain the cuff 10 in an annular shape, a curler (not illustrated) having appropriate flexibility may be provided in the cuff 10.

The sphygmomanometer main body 20 is integrally attached to a substantially central portion in a longitudinal direction of the cuff 10 having a band shape. In the embodiment, a portion to which the sphygmomanometer main body 20 is attached is supposed to correspond to a palmar surface (surface on the palm side) 410a of the left wrist 410.

The sphygmomanometer main body 20 has a flat and substantially rectangular parallelepiped shape along an outer peripheral surface of the cuff 10, and is formed to be small and thin so as not to disturb sleep of the subject 400. A corner portion connecting an upper surface of the sphygmomanometer main body 20 illustrated in FIG. 1 and a side surface surrounding the upper surface is chamfered in a curved shape.

As illustrated in FIG. 1, a sphygmomanometer display unit 30 forming a display screen is provided on an upper surface on the side farthest from the left wrist 410 of an outer surface of the sphygmomanometer main body 20. Further, a sphygmomanometer operation unit 40 for inputting an instruction from the subject 400 is provided on the upper surface and a side surface on the front side in the diagram.

In the embodiment, the sphygmomanometer display unit 30 includes a liquid crystal display (LCD), and is configured to display predetermined information, for example, a maximal blood pressure (unit; mmHg), a minimal blood pressure (unit; mmHg), and a pulse (units; beats per minute) in accordance with a control signal from a sphygmomanometer central processing unit (CPU) 110. Note that the sphygmomanometer display unit 30 may be either an organic EL display or a light emitting diode (LED).

The sphygmomanometer operation unit 40 has a plurality of buttons or switches operated by the subject 400. In the embodiment, the sphygmomanometer operation unit 40 includes a blood pressure measurement start switch 42A for the subject 400 to input a blood pressure measurement instruction in the normal blood pressure measurement mode, a nighttime measurement switch (mode operation unit) 42B for the subject 400 to input a blood pressure measurement instruction in the nighttime blood pressure measurement mode, and a communication switch 42C for the subject 400 to input a communication instruction between the sphygmomanometer 100 and the smartphone 200. The blood pressure measurement start switch 42A functions as a switch that stops blood pressure measurement being executed when the switch is pressed during the blood pressure measurement.

In description below, "normal blood pressure measurement" refers to blood pressure measurement started immediately after the blood pressure measurement start switch 42A is turned on. Further, in description below, "nighttime blood pressure measurement" refers to blood pressure measurement automatically performed according to a predetermined schedule, for example, during sleep of the subject 400 on the basis of an instruction input through the nighttime measurement switch 42B. The predetermined schedule refers to a type of schedule in which blood pressure measurement is started at predetermined time intervals such as two hours and four hours from a time (instruction time) when the nighttime measurement switch 42B is pressed, for example.

In the embodiment, both the blood pressure measurement switch 42A and the nighttime measurement switch 42B are momentary type (self-return type) switches, and are configured to be turned on only while being pushed down, and to be returned to an off state when being released.

Figure 3:
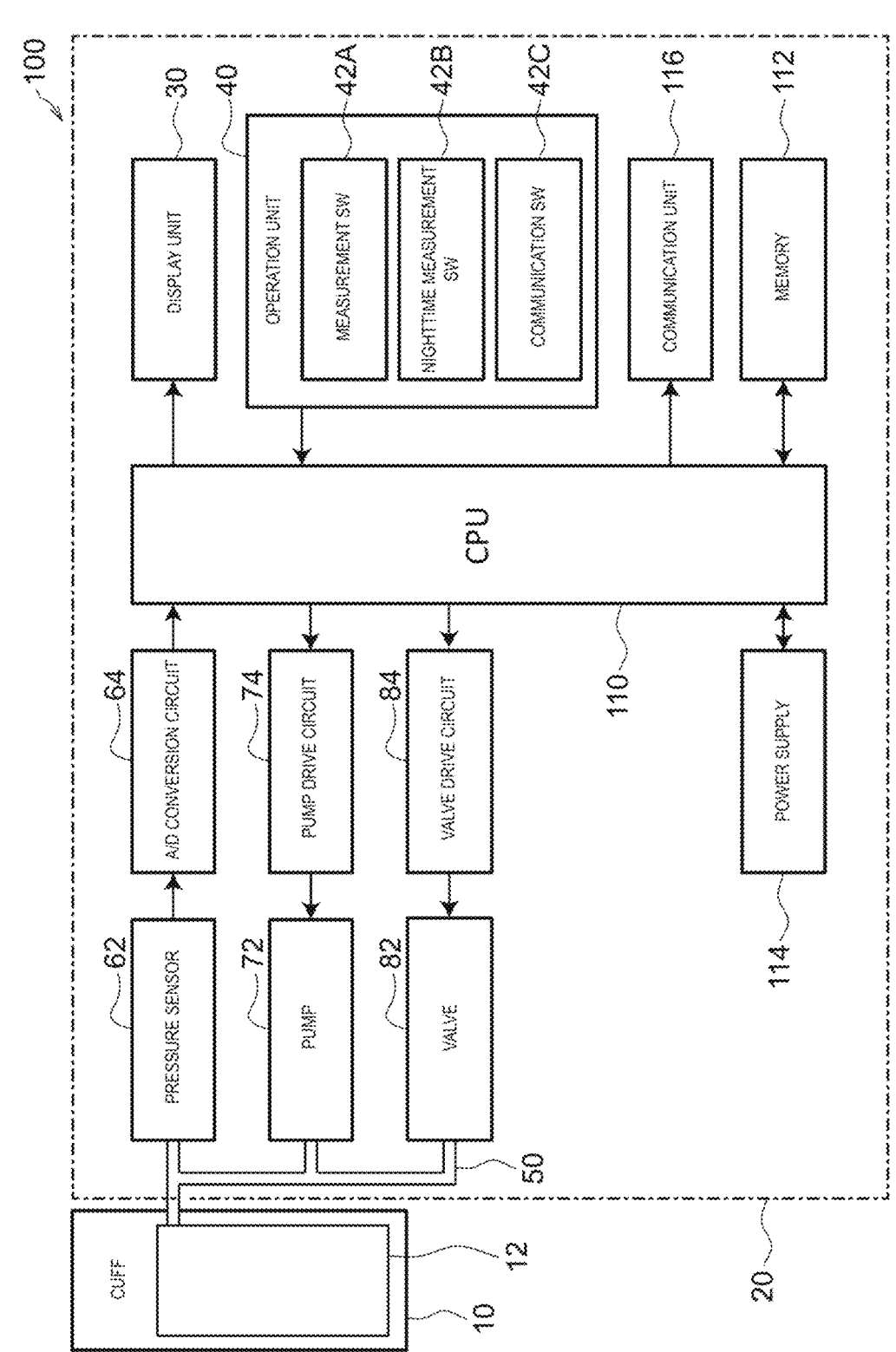
FIG. 3 is a block diagram of the wrist-type sphygmomanometer illustrated in FIG. 1.

FIG. 3 illustrates a block configuration of the sphygmomanometer 100.

The air bag 12 included in the cuff 10 described above and various fluid control devices (described below) included in the sphygmomanometer main body 20 are connected by an air pipe 50 in a manner that a fluid can circulate.

In addition to the sphygmomanometer display unit 30 and the sphygmomanometer operation unit 40 described above, the sphygmomanometer main body 20 includes the sphygmomanometer CPU 110 that is a control unit, a sphygmomanometer memory 112 that is a storage unit, a sphygmomanometer power supply unit 114, a sphygmomanometer communication unit 116 that performs BLE communication with the smartphone 200, a pressure sensor 62, a pump 72, and a valve 82. Further, the sphygmomanometer main body 20 includes an A/D conversion circuit 64 that converts output of the pressure sensor 62 from an analog signal to a digital signal, a pump drive circuit 74 that drives the pump 72, and a valve drive circuit 84 that drives the valve 82. The pressure sensor 62, the pump 72, and the valve 82 are connected to the air bag 12 through the air pipe 50 in a manner that a fluid can circulate.

The sphygmomanometer memory (storage unit) 112 stores a program for controlling the sphygmomanometer 100, data used to control the sphygmomanometer 100, setting data for setting various functions of the sphygmomanometer 100, a nighttime blood pressure measurement data set including a date, a day of the week, a measurement time, and a blood pressure value (including a maximal blood pressure, a minimal blood pressure, and a pulse) of the nighttime blood pressure measurement described later, and the like. The sphygmomanometer memory 112 is also used as a work memory that temporarily stores various types of information during program execution. In particular, the sphygmomanometer memory 112 according to the embodiment is configured as a program storage unit, and stores a normal blood pressure measurement program and a nighttime blood pressure measurement program for calculating blood pressure by an oscillometric method to be described later, and a transmission program for transmitting a nighttime blood pressure measurement data set to be described later to the smartphone 200.

The sphygmomanometer CPU 110 is configured to control operation of the entire sphygmomanometer 100. Specifically, the sphygmomanometer CPU 110 is configured as a pressure control unit that drives the pump 72 or the valve 82 according to a program for controlling the sphygmomanometer 100 stored in the sphygmomanometer memory 112, and a measurement implementation unit that performs blood pressure measurement by a normal blood pressure measurement program or a nighttime blood pressure measurement program to be described later. The sphygmomanometer CPU 110 also displays a blood pressure value obtained by performing blood pressure measurement on the sphygmomanometer display unit 30, and in particular, integrates a date, a day of the week, a measurement time, and a blood pressure value (including a maximal blood pressure, a minimal blood pressure, and a pulse) of the nighttime blood pressure measurement to store the data in the sphygmomanometer memory 112 as one nighttime blood pressure measurement data set.

In the embodiment, the sphygmomanometer power supply unit 114 includes a secondary battery, and is configured to supply power to each unit of the sphygmomanometer CPU 110, the pressure sensor 62, the pump 72, the valve 82, the sphygmomanometer display unit 30, the sphygmomanometer memory 112, the sphygmomanometer communication unit 116, the A/D conversion circuit 64, the pump drive circuit 74, and the valve drive circuit 84. The sphygmomanometer power supply unit 114 is also configured to be able to switch between on and off states, and becomes in the on state when the blood pressure measurement switch 42A is continuously pressed for three seconds or more, for example, in the off state.

The sphygmomanometer communication unit 116 performs BLE communication with the smartphone 200, and transmits, for example, a nighttime blood pressure measurement data set to the smartphone 200.

The pump 72 is configured to supply air as a fluid to the air bag 12 through the air pipe 50 in order to increase the pressure in the air bag 12 built in the cuff 10. The valve 82 is configured to discharge air in the air bag 12 through the air pipe 50 by opening or hold cuff pressure by closing in order to control the cuff pressure. The pump drive circuit 74 is configured to drive the pump 72 based on a control signal provided from the sphygmomanometer CPU 110. The valve drive circuit 84 is configured to open and close the valve 82 based on a control signal provided from the sphygmomanometer CPU 110.

The pressure sensor 62 and the A/D conversion circuit 64 are configured to detect cuff pressure. The pressure sensor 62 in the embodiment is a piezoresistive pressure sensor, and detects and outputs the cuff pressure of the air bag 12 as electric resistance due to a piezoresistive effect. The A/D conversion circuit 64 converts output (electric resistance) of the pressure sensor 62 from an analog signal to a digital signal and outputs the digital signal to the sphygmomanometer CPU 110. In the embodiment, the sphygmomanometer CPU 110 acquires the cuff pressure according to the electric resistance output from the pressure sensor 62.

[Blood Pressure Measurement Program]

The blood pressure measurement program calculates blood pressure of the subject 400 with the sphygmomanometer main body 20 attached to the left wrist 410. The blood pressure measurement program includes a normal blood pressure measurement program and a nighttime blood pressure measurement program. The normal blood pressure measurement program assumes that the subject 400 sits on a chair or the like and keeps the left wrist 410 to which the sphygmomanometer main body 20 is attached at the same height as the heart of the subject 400. The nighttime blood pressure measurement program assumes that the subject 400 lies on a bed or the like, and the left wrist 410 to which the sphygmomanometer main body 20 is attached is placed at a position lower than the heart of the subject 400. It is known that different blood pressure values are calculated when a relationship between the height of the sphygmomanometer main body 20 and the height of the heart of the subject 400 is different. For this reason, in the normal blood pressure measurement program and the nighttime blood pressure measurement program, a parameter used for blood pressure calculation is adjusted in advance in consideration of a relationship between the height of the sphygmomanometer main body 20 and the height of the heart of the subject 400 assumed by the programs. In particular, the nighttime blood pressure measurement program integrates a date, a day of the week, a measurement time, and a calculated blood pressure value (including a maximal blood pressure, a minimal blood pressure, and a pulse) of the nighttime blood pressure measurement to store the data in the sphygmomanometer memory 112 as one nighttime blood pressure measurement data set.

In the embodiment, in a schedule of the nighttime blood pressure measurement, the nighttime blood pressure measurement program is executed every two hours (time interval) after the nighttime measurement switch 42B is pressed and the sphygmomanometer 100 is set to the nighttime blood pressure measurement mode. In a mode in which a time at which the nighttime blood pressure measurement is performed is calculated based on a time point at which the nighttime measurement switch 42B is pressed, the nighttime blood pressure measurement program includes a program (not illustrated) that determines a measurement time, and a measurement time is determined based on the time determination program.

In the embodiment, as the measurement time of the nighttime blood pressure measurement, a time at every two hours elapsed from a time at which the sphygmomanometer 100 is set to the nighttime blood pressure measurement mode (instruction time) is set. However, the measurement time is not limited to this content, and for example, only a time at every one hour elapsed or a time after four hours elapsed may be set.

When performing the normal blood pressure measurement program or the nighttime blood pressure measurement program, the sphygmomanometer CPU 110 obtains a pulse wave signal from a fluctuation component of a pulse wave included in cuff pressure obtained by the pressure sensor 62, and calculates a blood pressure value (maximal blood pressure and minimal blood pressure) by using each program stored in the sphygmomanometer memory 112.

[Transmission Program]

In a nighttime blood pressure measurement data set stored in the sphygmomanometer memory 112, a transmission completion flag for distinguishing between "transmitted" and "not transmitted" is added in addition to a date, a day of the week, a measurement time, and a blood pressure value (including a maximal blood pressure, a minimal blood pressure, and a pulse) of the nighttime blood pressure measurement that is performed. The term "transmitted"

indicates that the nighttime blood pressure measurement data set has already been transmitted by the transmission program. The term "not transmitted" indicates that the nighttime blood pressure measurement data set has not yet been transmitted.

When transmitting the nighttime blood pressure measurement data set to the smartphone 200, the transmission program checks the transmission completion flag of each nighttime blood pressure measurement data set, and transmits a nighttime blood pressure measurement data set that has not been transmitted by the sphygmomanometer communication unit 116. In this manner, since a transmitted nighttime blood pressure measurement data set is not redundantly transmitted, size of a transmitted nighttime blood pressure measurement data set does not become excessively large. The transmission program also continues to repeatedly transmit the nighttime blood pressure measurement data set that has not been transmitted to the smartphone 200 until one hour elapses from the start of transmission. In this manner, for example, even when the smartphone 200 is in a situation of not being able to temporarily communicate, the nighttime blood pressure measurement data set that has not been transmitted is reliably transmitted. After one hour elapses from the start of transmission of the nighttime blood pressure measurement data set that has not been transmitted, the transmission program stops the transmission by the sphygmomanometer communication unit 116, and changes the transmission completion flag of the nighttime blood pressure measurement data set from "not transmitted" to "transmitted".

When receiving a communication instruction between the sphygmomanometer 100 and the smartphone 200, the sphygmomanometer CPU 110 executes the transmission program and continues to repeatedly transmit the nighttime blood pressure measurement data set that has not been transmitted to the smartphone 200 by the sphygmomanometer communication unit 116 until one hour elapses from the start of transmission.

[Configuration of Information Terminal]

As illustrated in FIG. 1, the smartphone 200 includes a smartphone main body 20, and a smartphone display unit (notification unit) 220 and a smartphone operation unit 230 provided on an upper surface of the smartphone main body 210 illustrated in the diagram. The smartphone 200 is also installed with application software for displaying information of the nighttime blood pressure measurement data set transmitted from the sphygmomanometer 100. The application software includes a receiving program for receiving information regarding a measurement time to be described later from the sphygmomanometer 100, a reminding time setting program for setting a reminding time at which the sphygmomanometer 100 should be set to the nighttime blood pressure measurement mode to be described later, and a reminding program for notifying the subject 400 that the sphygmomanometer 100 should be set to the nighttime blood pressure measurement mode at the reminding time to be described later.

In the embodiment, the smartphone display unit 220 includes a liquid crystal display (LCD), and is configured to display, for example, a date, a day of the week, a measurement time, and a blood pressure value (including a maximal blood pressure, a minimal blood pressure, and a pulse) of blood pressure measurement included in the nighttime blood pressure measurement data set transmitted from the sphygmomanometer 100, and a reminding time at which the sphygmomanometer 100 should be set to the nighttime blood pressure measurement mode according to a control signal from a smartphone central processing unit (CPU) 240 to be described later. Note that the smartphone display unit 220 may be either an organic EL display or a light emitting diode (LED).

In the embodiment, the smartphone operation unit 230 includes a touch panel provided in the smartphone display unit 220. Note that the smartphone operation unit 230 may be a hardware operation device such as a keyboard.

Figure 4:
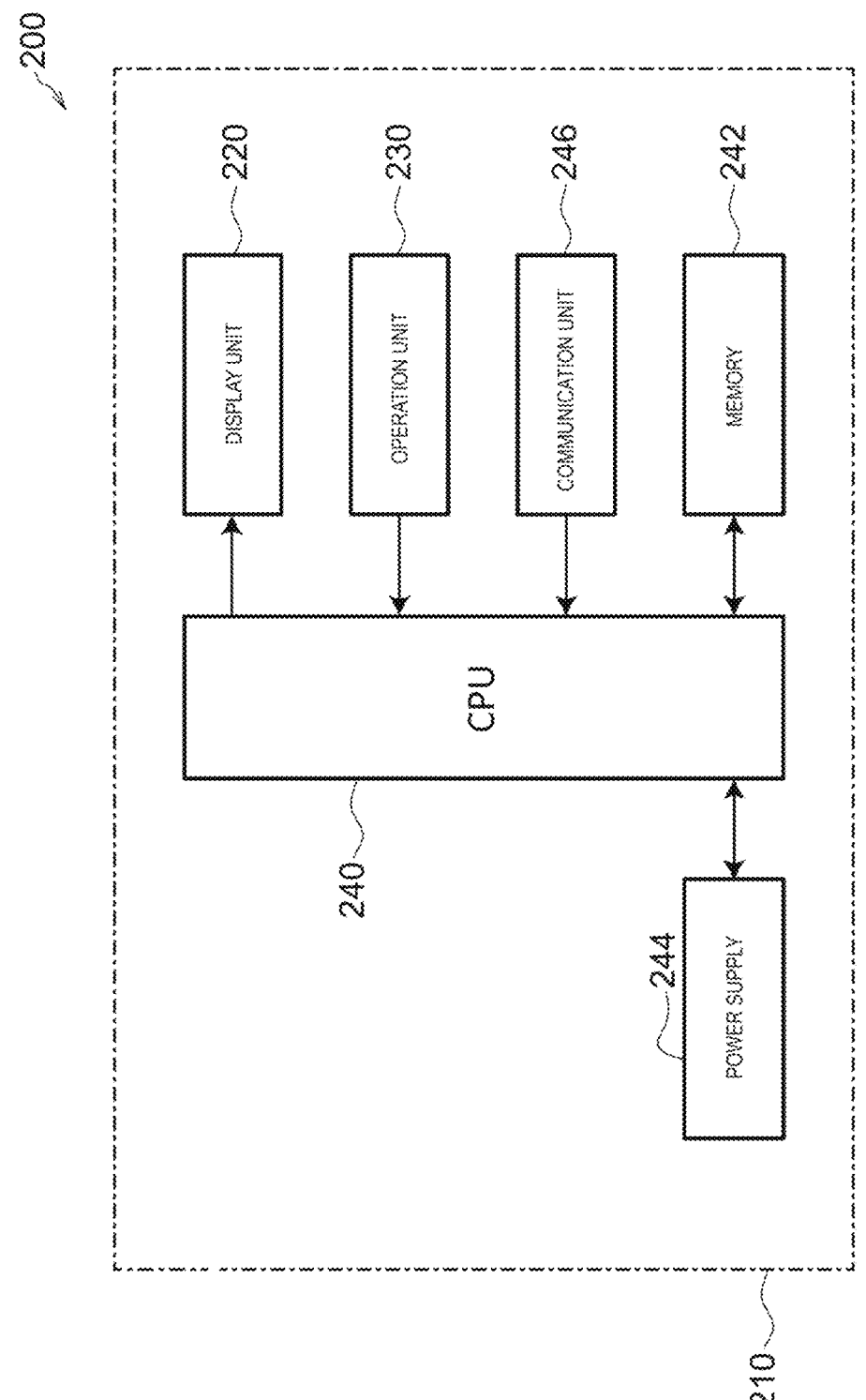
FIG. 4 is a block diagram of the smartphone illustrated in FIG. 1.

FIG. 4 illustrates a block configuration of the smartphone 200.

In addition to the smartphone display unit 220 and the smartphone operation unit 230 described above, the smartphone main body 210 includes the smartphone CPU 240 as a control unit, a smartphone memory 242 as a storage unit, a smartphone power supply unit 244, and a smartphone communication unit (information terminal communication unit) 246 that performs BLE communication with the sphygmomanometer 100.

The smartphone memory (storage unit) 242 stores a program for controlling the smartphone 200, data used for controlling the smartphone 200, setting data for setting various functions of the smartphone 20C, a nighttime blood pressure measurement data set (including a date, a day of the week, a measurement time, and a blood pressure value of blood pressure measurement) transmitted from the sphygmomanometer 100, and the like. The smartphone memory 242 is also used as a work memory that temporarily stores various types of information during program execution. In particular, the smartphone memory 242 according to the embodiment is configured as a program storage unit, and stores a receiving program, a reminding time setting program, and a reminding program, which will be described later, included in the application software. Further, as a storage medium of an auxiliary storage device for assisting a storage area of the smartphone memory 242, for example, a semiconductor memory (memory card, solid state drive (SSD)) may be used.

The smartphone CPU 240 is configured to control operation of the entire smartphone 200. Specifically, the smartphone CPU 240 is configured as a smartphone control unit that controls each unit of the smartphone 200 according to a program for controlling the smartphone 200 stored in the smartphone memory 242, a smartphone program execution unit that executes a program stored in the smartphone memory 242, and a reminding time calculation unit that calculates a reminding time at which the sphygmomanometer 100 is to be set to the nighttime blood pressure measurement mode by a reminding time setting program to be described later. The smartphone CPU 240 also displays, on the smartphone display unit 220, that the sphygmomanometer 100 should be set to the nighttime blood pressure measurement mode at a reminding time set by calculating a reminding time.

In the embodiment, the smartphone power supply unit 244 includes a secondary battery, and is configured to supply power to each unit of the smartphone CPU 240, the smartphone display unit 220, the smartphone operation unit 230, the smartphone memory 242, and the smartphone communication unit 246. The smartphone power supply unit 244 is also configured to be able to switch between on and off states.

The smartphone communication unit 246 performs BLE communication with the sphygmomanometer 100, and receives, for example, a nighttime blood pressure measurement data set from the sphygmomanometer 100.

[Receiving Program]

When the smartphone power supply unit 244 is on, the receiving program is automatically executed in the background by the smartphone CPU 240, and attempts to receive a nighttime blood pressure measurement data set transmitted from the sphygmomanometer 100 every minute by the smartphone communication unit 246. In this manner, when the smartphone power supply unit 244 is on, the subject 400 can reliably receive a nighttime blood pressure measurement data set transmitted from the sphygmomanometer 100 without performing a special operation on the smartphone operation unit 230. The receiving program also causes the received nighttime blood pressure measurement data set to be stored in the smartphone memory 242.

When the smartphone power supply unit 244 is on, the smartphone CPU 240 automatically executes the receiving program in the background, and attempts to receive a nighttime blood pressure measurement data set transmitted from the sphygmomanometer 100 every minute by the smartphone communication unit 246.

[Reminding Time Setting Program]

In the embodiment, when the receiving program receives a nighttime blood pressure measurement data set in a state where the application software installed in the smartphone 200 is activated, the reminding time setting program is executed. The reminding time setting program extracts a nighttime blood pressure measurement data set with an earliest measurement time for each blood pressure measurement date from a plurality of nighttime blood pressure measurement data sets stored in the smartphone memory 242. According to the above-described nighttime blood pressure measurement program, a measurement time of the nighttime blood pressure measurement is set every two hours from a time at which the sphygmomanometer 100 is set to the nighttime blood pressure measurement mode, that is, a time at which the nighttime measurement switch 42B is pressed. Therefore, the reminding time setting program calculates an instruction time at which the sphygmomanometer 100 is set to the nighttime blood pressure measurement mode by subtracting two hours from an earliest measurement time for each date of the nighttime blood pressure measurement. Note that the time subtracted from the earliest measurement time is not limited to two hours, and depends on a time interval set between a time at which the sphygmomanometer 100 is set to the nighttime blood pressure measurement mode and a measurement time when the measurement time is determined based on the time at which the sphygmomanometer 100 is set to the nighttime blood pressure measurement mode.

Next, the reminding time setting program classifies the calculated instruction time for each day of the week of the blood pressure measurement, extracts the predetermined number of latest instruction times, for example, latest five instruction times for each day of the week of the blood pressure measurement, and performs statistical processing to obtain an average instruction time. Using the average instruction time, a reminding time at which the sphygmomanometer 100 should be set to the nighttime blood pressure measurement mode is calculated.

In the embodiment, the reminding time is calculated by Mathematical Expression 1 below. However, this mathematical expression is merely an example, and the reminding time may be defined in another mathematical expression.

$$(\text{Reminding time}) = (\text{Average instruction time}) - 3 \times (\text{Standard deviation of extracted instruction time}) \quad (\text{Mathematical Expression 1})$$

The reminding time setting program extracts latest five instruction times to calculate an average of the instruction times (average instruction time) according to Mathematical Expression 1, and calculates the reminding time by subtracting three times the standard deviation of the extracted instruction times (margin time) from the calculated average instruction time. In this manner, the reminding time is set to an appropriate time zone. Further, since the reminding time is statistically processed based on a measurement time of the blood pressure measurement performed on the subject 400 in actual past nighttime blood pressure measurement, particularly in latest nighttime blood pressure measurement, a current lifestyle of the subject 400 is reflected in the reminding time.

[Reminding Program]

In the embodiment, when the calculated reminding time comes, the reminding program is executed. This reminding program displays letters "Please set nighttime blood pressure measurement mode" on the smartphone display unit 220.

When the receiving program receives a nighttime blood pressure measurement data set in a state in which the application software installed in the smartphone 200 is activated, the smartphone CPU 240 executes the reminding time setting program to calculate an instruction time at which the sphygmomanometer 100 is set to the nighttime blood pressure measurement mode. Next, the smartphone CPU 240 classifies the calculated instruction time for each day of the week of the blood pressure measurement according to the reminding time setting program, extracts the predetermined number of latest instruction times, for example, latest five instruction times for each day of the week of the blood pressure measurement to perform statistical processing, and calculates the reminding time at which the sphygmomanometer 100 should be set to the nighttime blood pressure measurement mode according to Mathematical Expression 1. After the above, the smartphone CPU 240 displays letters "Please set the nighttime blood pressure measurement mode" on the smartphone display unit 220 at the calculated reminding time according to the reminding program. Therefore, according to the blood pressure measurement system 300, the subject 400 is less likely to forget the operation.

[Nighttime Blood Pressure Measurement Mode]

The nighttime blood pressure measurement will be described. When the subject 400 who has not slept yet presses the nighttime measurement switch 42B of the sphygmomanometer main body 20 once in a state where the cuff 10 of the sphygmomanometer 100 is wound around the left wrist 410 of the subject 400, a blood pressure measurement instruction in the nighttime blood pressure measurement mode is output to the sphygmomanometer CPU 110.

After the above, a measurement time is set from the time at which the nighttime measurement switch 42B is pressed, and the nighttime blood pressure measurement program is executed according to the set measurement time. However, when the nighttime measurement switch 42B is pushed down again during the time until the sphygmomanometer 100 performs blood pressure measurement of the subject 400 in sleep in the nighttime (for example, within waiting time until a time at which a predetermined nighttime blood pressure measurement program is executed), the nighttime blood pressure measurement is instructed to stop, and the nighttime blood pressure measurement program is not executed.

Figure 5:
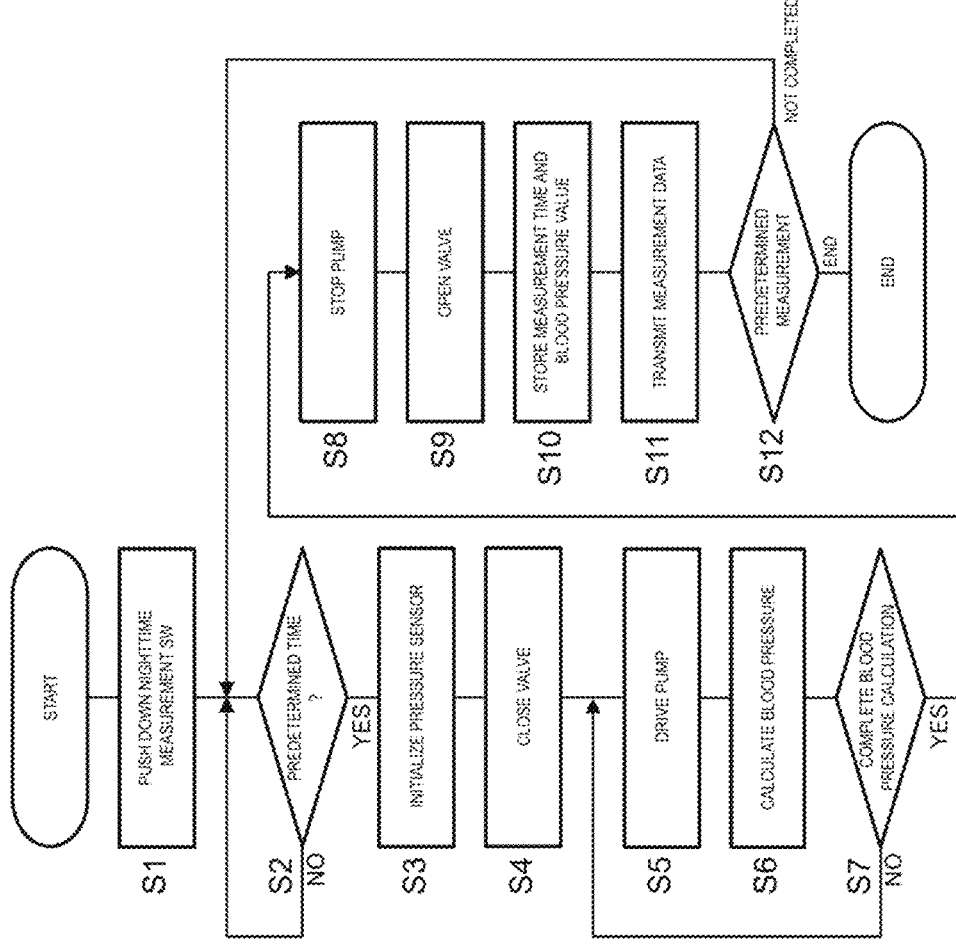
FIG. 5 is a flowchart of nighttime blood pressure measurement performed by the wrist-type sphygmomanometer illustrated in FIG. 1.

FIG. 5 illustrates an operation process when the subject 400 performs the nighttime blood pressure measurement by the sphygmomanometer 100. During the nighttime blood pressure measurement, the subject 400 wearing the sphygmomanometer 100 on the left wrist 410 remains to be in a state of lying on a bed or the like.

In this state, as shown in Step S1 of FIG. 5, when the subject 400 presses the nighttime measurement switch 42B provided in the sphygmomanometer main body 20 to input a blood pressure measurement instruction in the nighttime blood pressure measurement mode, the sphygmomanometer CPU 110 sets a measurement time and then determines whether or not it is the measurement time (Step S2). If it is not the measurement time (when the process proceeds to NO in Step S2), the sphygmomanometer CPU 110 waits until the measurement time comes.

When it is the measurement time (when the process proceeds to YES in Step S2), the sphygmomanometer CPU 110 initializes the pressure sensor 62 (Step S3). Specifically, the sphygmomanometer CPU 110 initializes a processing memory area, stops the pump 72, and performs 0 mmHg adjustment (setting the atmospheric pressure to 0 mmHg) of the pressure sensor 62 in a state where the valve 82 is opened.

Next, the sphygmomanometer CPU 110 closes the valve 82 via the valve drive circuit 84 (Step S4), and then drives the pump 72 via the pump drive circuit 74 to start pressurization of the cuff 10 (air bag 12) (Step S5). At this time, the sphygmomanometer CPU 110 controls a pressurization rate of cuff pressure, which is pressure in the air bag 12, based on output of the pressure sensor 62 while supplying air from the pump 72 to the air bag 12 through the air pipe 50.

Next, in Step S6, the sphygmomanometer CPU 110 calculates a blood pressure value (maximal blood pressure and minimal blood pressure) by using the above-described nighttime blood pressure measurement program stored in the sphygmomanometer memory 112 based on a pulse wave signal acquired at this time point.

At this time point, in a case where the blood pressure value cannot be calculated yet due to insufficient data (in a case where the process proceeds to NO in Step S7), the sphygmomanometer CPU 110 repeats the processing of Steps S5 and S6 unless the cuff pressure reaches an upper limit pressure (which is predetermined for safety at, for example, 300 mmHg).

When the blood pressure value is calculated (in a case where the process proceeds to YES in Step S7), the sphygmomanometer CPU 110 performs control to stop the pump 72 (Step SB), open the valve 82 (Step S9), and exhaust the air in the cuff 10 (air bag 12).

After the above, the sphygmomanometer CPU 110 displays the calculated blood pressure value on the sphygmomanometer display unit 30, and performs control to store a date, a day of the week, a measurement time, and a blood pressure value of the nighttime blood pressure measurement program as a nighttime blood pressure measurement data set in the sphygmomanometer memory 112 (Step S10).

Next, the sphygmomanometer CPU 110 checks the transmission completion flag of a nighttime blood pressure measurement data set stored in the sphygmomanometer memory 112 by the above-described transmission program, and transmits a nighttime blood pressure measurement data set that has not been transmitted, for example, the nighttime blood pressure measurement data set stored in Step S10 to the smartphone 200 by the sphygmomanometer communication unit 116 (Step S11). The sphygmomanometer CPU 110 also continues to repeatedly transmit the nighttime blood pressure measurement data set that has not been transmitted to the smartphone 200 until one hour elapses from the start of transmission, stops the transmission by the sphygmomanometer communication unit 116 after one hour elapses from the start of transmission, and changes the transmission completion flag of the nighttime blood pressure measurement data set from "not transmitted" to "transmitted".

When one time of blood pressure measurement set in the schedule described above is completed, the sphygmomanometer CPU 110 determines whether blood pressure measurement at all set measurement times is completed (Step S12). In a case where the blood pressure measurement at this measurement time is still scheduled (when the process proceeds to "not completed" in Step S12), the sphygmomanometer CPU 110 returns to Step S2 and determines whether it is a next set measurement time. If it is not the measurement time (when the process proceeds to NC in Step S2), the sphygmomanometer CPU 110 waits until the measurement time comes.

When it is the next set measurement time (when the process proceeds to YES in Step S2), the sphygmomanometer CPU 110 repeats the processing of Steps S3 to S11, and again determines in Step S12 whether the blood pressure measurement at all the set measurement times has been completed.

When the blood pressure measurement at all the set measurement times is completed (when the process proceeds to "end" in Step S12), the sphygmomanometer CPU 110 ends the nighttime blood pressure measurement.

[First Reminding Method]

A first reminding method for notifying the subject 400 that the sphygmomanometer 100 should be set to the nighttime blood pressure measurement mode at the reminding time at which the sphygmomanometer 100 should be set to the nighttime blood pressure measurement mode will be described. When the subject 400 turns on the smartphone 200 while the application software including the receiving program, the reminding time setting program, and the reminding program is installed in the smartphone 200, the receiving program is executed in the background. Further, when the subject 400 activates the application software by using the smartphone operation unit 230, an initial value of the reminding time is set to, for example, 22:00 PM.

After the above, when the sphygmomanometer 100 is set to the nighttime blood pressure measurement mode and the nighttime blood pressure measurement program is executed in a state in which the application software is activated, the smartphone 200 receives a nighttime blood pressure measurement data set from the sphygmomanometer 100 and the reminding time setting program is executed. As described above, the reminding time setting program extracts a nighttime blood pressure measurement data set having an earliest measurement time for each date of blood pressure measurement from a plurality of nighttime blood pressure measurement data sets stored in the smartphone memory 242, and calculates an instruction time at which the sphygmomanometer 100 is set to the nighttime blood pressure measurement mode. Next, the reminding time setting program classifies the calculated instruction time for each day of the week of the blood pressure measurement, extracts latest five instruction times for each day of the week of the blood pressure measurement to perform statistical processing, and calculates the reminding time at which the sphygmomanometer 100 should be set to the nighttime blood pressure measurement mode according to Mathematical Expression 1.

After the above, at the calculated reminding time, letters "Please set the nighttime blood pressure measurement mode" are displayed on the smartphone display unit 220.

Figure 6:
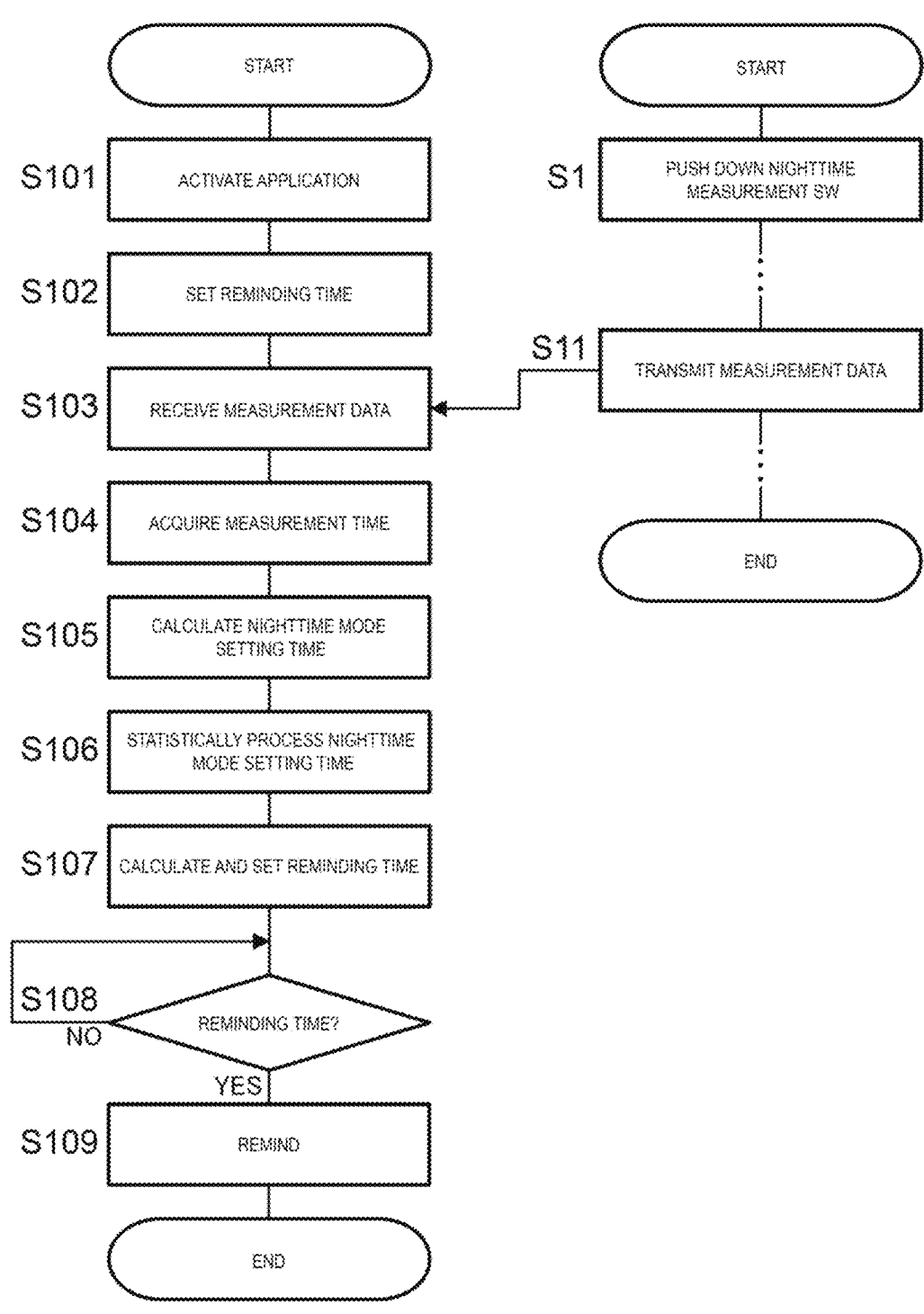
FIG. 6 is a first flowchart of the blood pressure measurement system illustrated in FIG. 1.

FIG. 6 illustrates an operation process of the first reminding method performed by the blood pressure measurement system 300. In particular, the left side of the diagram illustrates an operation process when the reminding time setting program and the reminding program included in the application software installed in the smartphone 200 are executed. In contrast, the right side of the diagram illustrates a part of the operation process when the subject 400 performs the nighttime blood pressure measurement with the sphygmomanometer 100 described with reference to FIG. 5. During this first reminding method, the smartphone 200 remains to be in an on state.

In this state, as illustrated in Step S101 of FIG. 6, when the application software installed in the smartphone 200 is activated, an initial value of the reminding time is set to, for example, 22:00 PM (Step S102).

After the above, the subject 400 sets the sphygmomanometer 100 to the above-described nighttime blood pressure measurement mode in a state where the application software of the smartphone 200 is activated and sleeps, and then, the nighttime blood pressure measurement is performed at the set measurement time. As described above, in Step S11, the sphygmomanometer CPU 110 checks the transmission completion flag of a nighttime blood pressure measurement data set stored in the sphygmomanometer memory 112 by the transmission program, and transmits a nighttime blood pressure measurement data set that has not been transmitted, for example, the nighttime blood pressure measurement data set stored in Step S10 to the smartphone 200 by the sphygmomanometer communication unit 116.

At this time, since the above-described receiving program is executed in the background of the smartphone 200, the smartphone CPU 240 receives the nighttime blood pressure measurement data set transmitted from the sphygmomanometer 100 by the smartphone communication unit 246 (Step S103). In this manner, the smartphone 200 receives the nighttime blood pressure measurement data set including the measurement time from the sphygmomanometer 100, and can calculate the reminding time from the measurement time by the smartphone CPU 240 that executes the reminding time setting program.

After the above, the smartphone CPU 240 performs control to store the received nighttime blood pressure measurement data set in the smartphone memory 242 (Step S104).

Next, the smartphone CPU 240 executes the above-described reminding time setting program to calculate an instruction time at which the sphygmomanometer 100 is set to the nighttime blood pressure measurement mode for each date of the blood pressure measurement of the nighttime blood pressure measurement data set stored in the smartphone memory 242 (Step S105).

After the above, the smartphone CPU 240 classifies the calculated instruction time for each day of the week of the blood pressure measurement according to the reminding time setting program described above, extracts latest five instruction times for each day of the week of the blood pressure measurement to perform statistical processing (Step S106), and calculates and sets the reminding time at which the sphygmomanometer 100 should be set to the nighttime blood pressure measurement mode according to Mathematical Expression 1 (Step S107). In this manner, since the reminding time is statistically processed based on the measurement time of the blood pressure measurement performed on the subject 400 in actual past nighttime blood pressure measurement, particularly latest nighttime blood pressure measurement, a time that is average and appropriate is set according to a current lifestyle of the subject 400.

After setting the reminding time, the smartphone CPU 240 determines whether or not it is the reminding time set for each day of the week by the reminding program (Step S108), and if it is not the reminding time (when the process proceeds to NO in Step S108), the smartphone CPU 240 waits until the reminding time comes.

When the reminding time comes (when the process proceeds to YES in Step S108), the smartphone CPU 240 outputs letters "Please set the nighttime blood pressure measurement mode" on the smartphone display unit 220 according to the above reminding program (Step S109).

After the above, the smartphone CPU 240 ends the notification to the subject 400 that the sphygmomanometer 100 should be set to the nighttime blood pressure measurement mode, but performs the operation process of Steps S108 and S109 with respect to a reminding time of the next day in the background.

According to the first reminding method described above, the blood pressure measurement system 300 appropriately sets the reminding time in accordance with the lifestyle of the subject 400 and notifies the reminding time to the subject 400 based on a measurement time of the blood pressure measurement performed on the subject 400 in the actual past nighttime blood pressure measurement mode. Further, the subject 400 can reliably receive the notification of "Please set (the sphygmomanometer 100 to) the nighttime blood pressure measurement mode" from the smartphone 200 possessed by the subject 400. Therefore, according to the blood pressure measurement system 300, the subject 400 is less likely to forget the operation.

Further, in the first reminding method described above, since the smartphone 200 is an information terminal possessed by the subject 400, the subject 400 can reliably receive a notification that the sphygmomanometer 100 should be set to the nighttime blood pressure measurement mode. Therefore, since the subject 400 can reliably grasp that the sphygmomanometer 100 should be set to the nighttime blood pressure measurement mode, the subject 400 is less likely to forget to set the sphygmomanometer 100 to the nighttime blood pressure measurement mode.

[Second Reminding Method]

A second reminding method for notifying the subject 400 that the sphygmomanometer 100 should be set to the nighttime blood pressure measurement mode at the reminding time at which the sphygmomanometer 100 should be set to the nighttime blood pressure measurement mode will be described. In the first reminding method, when the sphygmomanometer 100 is set to the nighttime blood pressure measurement mode and the nighttime blood pressure measurement program is executed, the smartphone 200 receives a nighttime blood pressure measurement data set from the sphygmomanometer 100. However, in the second reminding method, the subject 400 presses the communication switch 42C provided on the sphygmomanometer operation unit 40 and inputs a communication instruction between the sphygmomanometer 100 and the smartphone 200, so that the transmission program is executed and the smartphone 200 receives a nighttime blood pressure measurement data set from the sphygmomanometer 100. After the above, operation performed by the smartphone 200 is the same as that in the first reminding method.

Figure 7:
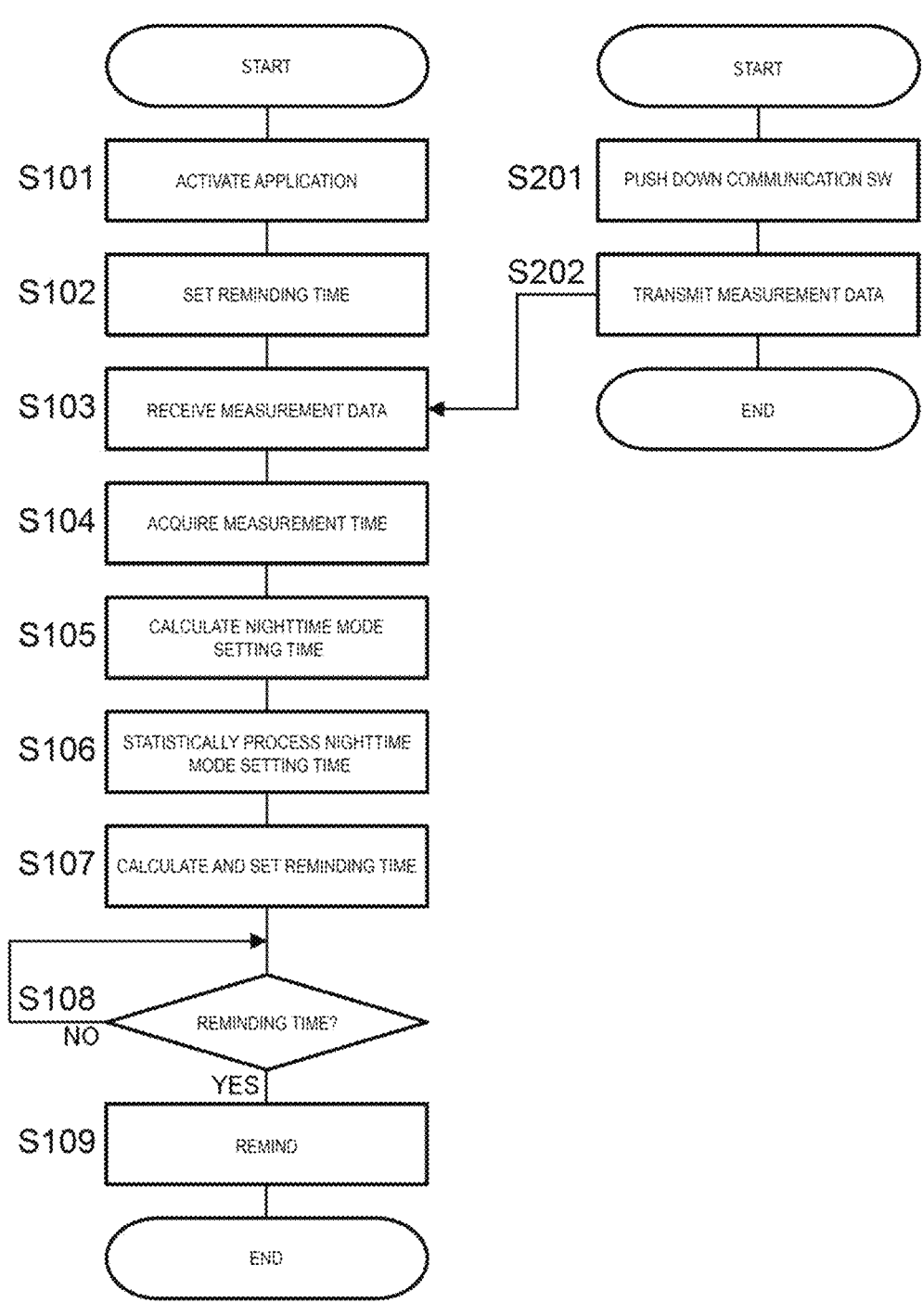
FIG. 7 is a second flowchart of the blood pressure measurement system illustrated in FIG. 1.

FIG. 7 illustrates an operation process of the second reminding method performed by the blood pressure measurement system 300. Like FIG. 6, the left side of the diagram illustrates an operation process when the reminding time setting program and the reminding program included in the application software installed in the smartphone 200 are executed. In contrast, the right side of the diagram illustrates an operation process in which the subject 400 presses the communication switch 42C and inputs a communication instruction between the sphygmomanometer 100 and the smartphone 200, so that the sphygmomanometer CPU 110 executes the transmission program and transmits a nighttime blood pressure measurement data set to the smartphone 200. During this second reminding method, the smartphone 200 remains to be in an on state.

In this state, as illustrated in Step S101 of FIG. 7, when the application software installed in the smartphone 200 is activated, an initial value of the reminding time is set to, for example, 22:00 PM (Step S102).

After the above, in a state where the application software of the smartphone 200 is activated, the subject 400 presses the communication switch 42C provided on the sphygmomanometer operation unit 40 to input a communication instruction between the sphygmomanometer 100 and the smartphone 200 (Step S201). In this manner, the sphygmomanometer CPU 110 checks the transmission completion flag of a nighttime blood pressure measurement data set stored in the sphygmomanometer memory 112 by the transmission program, and transmits a nighttime blood pressure measurement data set that has not been transmitted to the smartphone 200 by the sphygmomanometer communication unit 116 (Step S202).

At this time, since the above-described receiving program is executed in the background of the smartphone 200, the smartphone CPU 240 receives the nighttime blood pressure measurement data set transmitted from the sphygmomanometer 100 by the smartphone communication unit 246 (Step S103). The operation process in and after Step S103 is the same as that in the first reminding method.

With the above-described second reminding method, the subject 400 can manually transmit a nighttime blood pressure measurement data set stored in the sphygmomanometer memory 112 to the smartphone 200.

[Third Reminding Method]

A third reminding method for notifying the subject 400 that the sphygmomanometer 100 should be set to the nighttime blood pressure measurement mode at the reminding time at which the sphygmomanometer 100 should be set to the nighttime blood pressure measurement mode will be described. In the first reminding method, when the reminding program is executed once at the reminding time, the notification to the subject 400 of that the sphygmomanometer 100 should be set to the nighttime blood pressure measurement mode ends. in the third reminding method, a plurality of reminding times is set, and the reminding program is executed at each reminding time.

Figure 8:
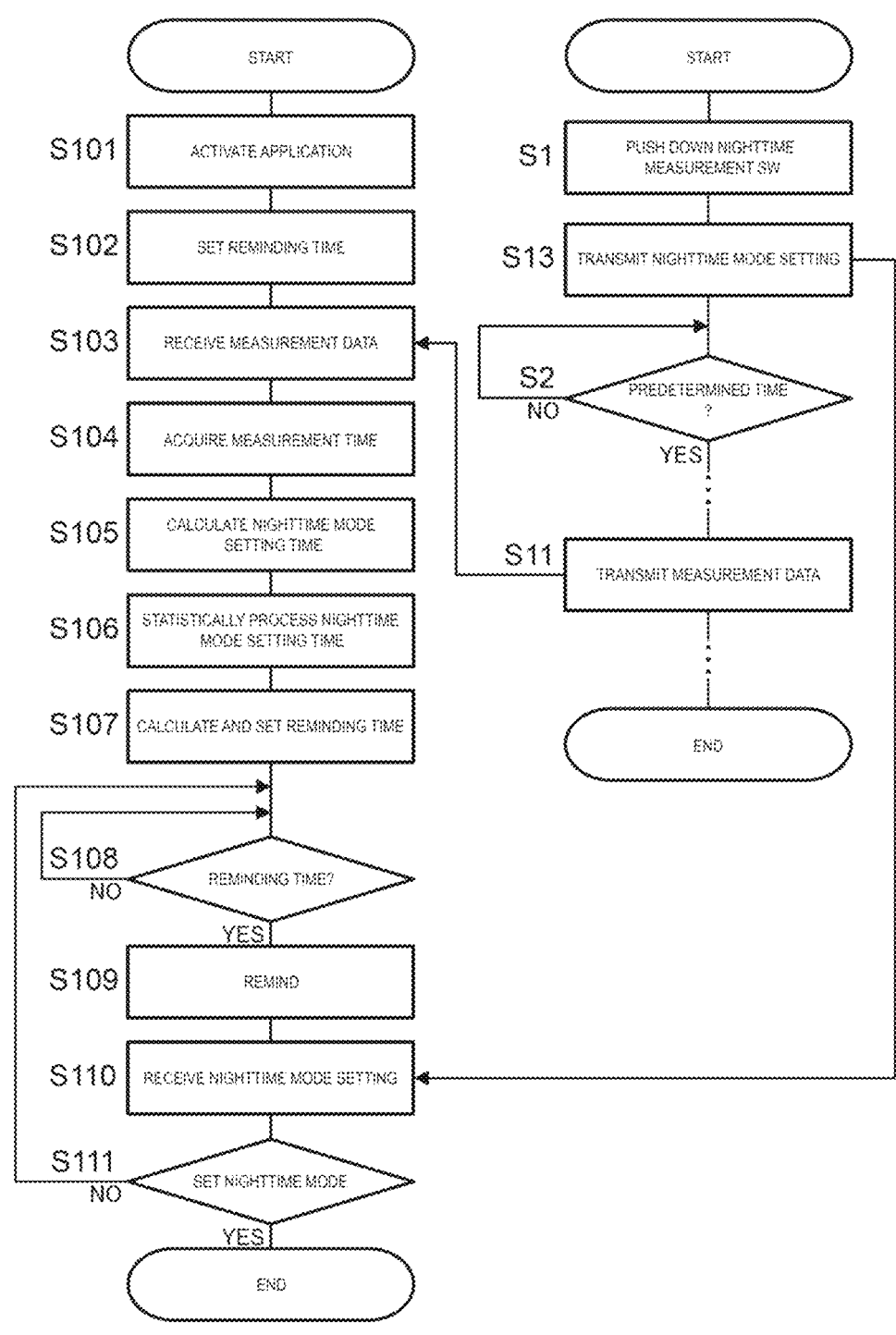
FIG. 8 is a third flowchart of the blood pressure measurement system illustrated in FIG. 1.

FIG. 8 illustrates an operation process of the third reminding method performed by the blood pressure measurement system 300. Like FIG. 6, the left side of the diagram illustrates an operation process when the reminding time setting program and the reminding program included in the application software installed in the smartphone 200 are executed. In contrast, the right side of the diagram illustrates a part of the operation process when the subject 400 performs the nighttime blood pressure measurement with the sphygmomanometer 100 like FIG. 6.

Steps S101 to S106 are performed similarly to the operation process illustrated in FIG. 6.

After the above, the smartphone CPU 240 resets the calculated reminding time (Step S107), and sets a predetermined number of times, for example, three times, for example, every five minutes based on the reminding time as a time (additional reminding time) at which repeated notification should be performed.

Next, Steps S108 and S109 are performed similarly to the operation process illustrated in FIG. 6.

In contrast, when the sphygmomanometer 100 is set to the nighttime blood pressure measurement mode, unlike the operation process illustrated in FIG. 5, in Step S1, the subject 400 presses the nighttime measurement switch 42B provided on the sphygmomanometer main body 20 to input a blood pressure measurement instruction of the nighttime blood pressure measurement mode, and then the sphygmomanometer CPU 110 transmits, to the smartphone 200, that the nighttime blood pressure measurement mode is set by the sphygmomanometer communication unit 116 (Step S13).

In Step S109, the smartphone CPU 240 receives, from the sphygmomanometer 100, that the sphygmomanometer 100 is set to the nighttime blood pressure measurement mode after outputting letters "Please set the nighttime blood pressure measurement mode" to the smartphone display unit 220 or while waiting until the reminding time comes (Step S110).

After the above, the smartphone CPU 240 determines whether or not the sphygmomanometer 100 is set to the nighttime blood pressure measurement mode (Step S111). In Step S110, when receiving from the sphygmomanometer 100 that the sphygmomanometer 100 is set to the nighttime blood pressure measurement mode, the smartphone CPU 240 determines that the sphygmomanometer 100 is set to the nighttime blood pressure measurement mode (proceeds to YES in Step S111), and disables the notification to the subject 400 that the sphygmomanometer 100 should be set to the nighttime blood pressure measurement mode at subsequent reminding times. In contrast, when the sphygmomanometer 100 has not received, from the sphygmomanometer 100, that the sphygmomanometer 100 is set to the nighttime blood pressure measurement mode, the smartphone CPU 240 determines that the sphygmomanometer 100 is not set to the nighttime blood pressure measurement mode (proceeds to NO in Step S111), returns to Step S108, determines whether or not it is a next set reminding time (additional reminding time), and if it is not the reminding time (when proceeding to NO in Step S108), the smartphone CPU 240 waits until the reminding time comes.

When it is the next set reminding time (when proceeding to YES in Step S108), the smartphone CPU 240 repeats the processing of Steps S109 to S110, and again determines whether or not the sphygmomanometer 100 is set to the nighttime blood pressure measurement mode in Step S111.

When the sphygmomanometer 100 is set to the nighttime blood pressure measurement mode or it is past all the reminding times, the smartphone CPU 240 ends notifying the subject 400 that the sphygmomanometer 100 should be set to the nighttime blood pressure measurement mode, but performs the operation process of Steps S108 to S111 with respect to a reminding time on the next day in the background.

According to the above-described third reminding method, even if the subject 400 cannot once receive the notification that the sphygmomanometer 100 should be set to the nighttime blood pressure measurement mode, the subject 400 can receive next and subsequent notifications.

Other Embodiments

In the above-described embodiment, the blood pressure measurement system 300 includes the smartphone 200 as an information terminal capable of communicating with the sphygmomanometer 100, but may include other personal digital assistants (PDAs) or wearable computing.

In the above-described embodiment, the smartphone 200 notifies the subject 400 that the sphygmomanometer 100 should be set to the nighttime blood pressure measurement mode by displaying letters "Please set to the nighttime blood pressure measurement mode" on the smartphone display unit 220. However, a notification sound generation unit and a vibration generation unit may be further provided to perform notification by using a notification sound, vibration, and the like.

In the above-described embodiment, the smartphone 200 notifies the subject 400 that the sphygmomanometer 100 should be set to the nighttime blood pressure measurement mode by displaying letters "Please set the nighttime blood pressure measurement mode" on the smartphone display unit 220. However, the sphygmomanometer 100 may also notify the subject 400 that the sphygmomanometer 100 should be set to the nighttime blood pressure measurement mode by displaying letters "Please set the nighttime blood pressure measurement mode" on the sphygmomanometer display unit 30. In this case, the sphygmomanometer 100 can preferably receive the reminding time set by the smartphone CPU 240 by the reminding time setting program.

In the above-described embodiment, the sphygmomanometer CPU 110 calculates blood pressure in a pressurization process of the cuff 10 (air bag 12), but may calculate the blood pressure in a depressurization process of the cuff.

In the above-described embodiment, the sphygmomanometer 100 includes the blood pressure measurement switch 42A to which a blood pressure measurement instruction in the normal blood pressure measurement mode is input and the nighttime measurement switch 42B to which a blood pressure measurement instruction in the nighttime blood pressure measurement mode is input. However, for example, a signal receiving unit of the sphygmomanometer receives the instruction from a smartphone or the like existing outside the sphygmomanometer via wireless communication, and the signal received by the signal receiving unit may be replaced with a signal output from the normal blood pressure measurement switch or the nighttime measurement switch to the sphygmomanometer CPU.

In the above-described embodiment, the sphygmomanometer 100 is configured such that the blood pressure measurement switch 42A outputs a signal of the blood pressure measurement instruction in the normal blood pressure measurement mode to the sphygmomanometer CPU 110, and the nighttime measurement switch 42B outputs a signal of the blood pressure measurement instruction in the nighttime blood pressure measurement mode to the sphygmomanometer CPU 110. However, for example, the configuration may be such that the blood pressure measurement switch is pressed once to output the signal of the blood pressure measurement instruction in the normal blood pressure measurement mode to the sphygmomanometer CPU, and the blood pressure measurement switch is pressed twice within a certain time to output the signal of the blood pressure measurement instruction in the nighttime blood pressure measurement mode to the sphygmomanometer CPU.

In the above-described embodiment, the sphygmomanometer main body 20 is integrally attached to the cuff 10, but may be provided separately from the cuff and connected to the cuff 10 (air bag 12) via a flexible air tube in a manner that a fluid can circulate.

In the above-described embodiment, the nighttime blood pressure measurement program, the transmission program, and a process of these programs are stored in the sphygmomanometer memory 112 as software, but may be recorded on a non-transitory medium such as a compact disc (CD), a digital universal disc (DVD), a flash memory, or the like. By installing software recorded in the above-described medium in a substantial computer device such as a personal computer, a personal digital assistant (PDA), or a smartphone, the above-described programs and process can be executed by the computer device.

As described above, a blood pressure measurement system of the present disclosure comprises a sphygmomanometer having a nighttime blood pressure measurement mode for automatically starting blood pressure measurement according to a predetermined schedule; and an information terminal communicable with the sphygmomanometer, wherein the sphygmomanometer includes a mode operation unit that inputs an instruction to set the sphygmomanometer to the nighttime blood pressure measurement mode, at least one of the sphygmomanometer and the information terminal includes:

a storage unit that stores measurement times at which blood pressure measurement was performed in the nighttime blood pressure measurement mode; and a reminding time calculation unit that calculates a reminding time at which a subject is notified of that the sphygmomanometer should be set to the nighttime blood pressure measurement mode based on the measurement times stored in the storage unit, and the information terminal includes a notification unit that notifies the subject that the sphygmomanometer should be set to the nighttime blood pressure measurement mode at the reminding time.

In the present description, the sphygmomanometer and the information terminal can typically communicate with each other in a state of being separated from each other.

Further, the "mode operation unit" may be, for example, a switch provided in a main body of the sphygmomanometer, and may receive switching on by the user as an instruction, or may be composed of a communication unit that receives an instruction from a smartphone or the like existing outside the sphygmomanometer via wireless communication.

Depending on a schedule, a next "reminding time" may be set in a time zone several hours before the "measurement time" at which the blood pressure measurement was performed. Here, the "measurement time" and the "reminding time" do not include a date and define only a time.

In the blood pressure measurement system of the present disclosure, for example, the subject inputs an instruction by the mode operation unit and sets the sphygmomanometer to the nighttime blood pressure measurement mode in which the blood pressure measurement is automatically started according to a predetermined schedule. The sphygmomanometer set to the nighttime blood pressure measurement mode automatically performs blood pressure measurement according to the schedule. At this time, the measurement time at which the blood pressure measurement was performed in the nighttime blood pressure measurement mode is stored in the storage unit provided in at least one of the sphygmomanometer and the information terminal. Further, the reminding time calculation unit is provided in at least one of the sphygmomanometer and the information terminal, and calculates a reminding time at which the subject is notified of that the sphygmomanometer should be set to the nighttime blood pressure measurement mode based on the measurement time stored in the storage unit. In contrast, the information terminal communicable with the sphygmomanometer notifies the subject that the sphygmomanometer should be set to the nighttime blood pressure measurement mode at the reminding time for the next nighttime blood pressure measurement by the notification unit. Upon receiving this notification, the subject operates the mode operation unit to input an instruction to set the sphygmomanometer to the nighttime blood pressure measurement mode. Therefore, according to this blood pressure measurement system, the subject is less likely to forget the operation.

The present disclosure provides the blood pressure measurement system according to one embodiment, wherein the schedule is a type of schedule in which blood pressure measurement is started at a predetermined time interval from an instruction time at which an instruction for setting the nighttime blood pressure measurement mode is input by the mode operation unit, and the reminding time calculation unit calculates the instruction time by subtracting the time interval from the measurement times, calculates an average instruction time by statistically processing the instruction time, and calculates the reminding time by subtracting a margin time from the average instruction time.

Here, the "predetermined time interval" is, for example, four hours.

Further, the "margin time" refers to, for example, three times the standard deviation of the average instruction time (3σ), or a certain period of time (for example, 30 minutes) including that.

In the blood pressure measurement system of this embodiment, the schedule is a type of schedule in which the blood pressure measurement is started at a predetermined time interval (for example, four hours) from an instruction time at which an instruction to set the nighttime blood pressure measurement mode is input by the mode operation unit. Therefore, the reminding time should be set in a time zone retrospective by the time interval from the measurement time at which the blood pressure measurement was performed. In view of the above, in the blood pressure measurement system according to this embodiment, the reminding time calculation unit calculates the instruction time by subtracting the time interval from the measurement time, calculates an average instruction time by statistically processing the instruction time, and calculates the reminding time by subtracting the margin time from the average instruction time. Therefore, the reminding time is set to an appropriate time zone. Further, since the reminding time is statistically processed based on a measurement time of the blood pressure measurement performed on the subject in actual past nighttime blood pressure measurement, a lifestyle of the subject is reflected in the reminding time.

The present disclosure provides the blood pressure measurement system according to one embodiment, wherein the notification unit repeats notification that the sphygmomanometer should be set to the nighttime blood pressure measurement mode until the sphygmomanometer is set to the nighttime blood pressure measurement mode after notifying that the sphygmomanometer should be set to the nighttime blood pressure measurement mode at the reminding time.

The subject may not be able to receive the notification that the sphygmomanometer should be set to the nighttime blood pressure measurement mode at the reminding time for various reasons such as not having the information terminal temporarily at hand. In view of the above, in the blood pressure measurement system of this embodiment, the notification unit repeats notification that the sphygmomanometer should be set to the nighttime blood pressure measurement mode until the sphygmomanometer is set to the nighttime blood pressure measurement mode after notifying that the sphygmomanometer should be set to the nighttime blood pressure measurement mode at the reminding time. In this manner, even if the subject cannot once receive the notification that the sphygmomanometer should be set to the nighttime blood pressure measurement mode at the reminding time, the subject can receive the notification for the next and subsequent times.

The present disclosure provides the blood pressure measurement system according to one embodiment, wherein the sphygmomanometer includes a sphygmomanometer communication unit capable of communicating with the information terminal and the storage unit, the information terminal includes an information terminal communication unit capable of communicating with the sphygmomanometer and the reminding time calculation unit, and the measurement times are transmitted from the sphygmomanometer communication unit of the sphygmomanometer to the information terminal communication unit of the information terminal.

In the blood pressure measurement system of this embodiment, the sphygmomanometer includes a sphygmomanometer communication unit capable of communicating with the information terminal. Further, the information terminal includes an information terminal communication unit capable of communicating with the sphygmomanometer. In this blood pressure measurement system, the measurement time is transmitted from the sphygmomanometer communication unit to the information terminal communication unit. In this manner, the information terminal receives the measurement time from the sphygmomanometer, and the reminding time calculation unit can calculate the reminding time from the measurement time.

The present disclosure provides the blood pressure measurement system according to one embodiment, wherein the reminding time calculation unit calculates the reminding time by using a predetermined number of latest ones of the measurement times.

In the blood pressure measurement system of this embodiment, the reminding time calculation unit calculates the reminding time by using a predetermined number of latest measurement times stored in the storage unit. Therefore, since the reminding time is based on the measurement time of the blood pressure measurement performed on the subject in latest nighttime blood pressure measurement, an appropriate time according to a current lifestyle of the subject is set.

The present disclosure provides the blood pressure measurement system according to one embodiment, wherein the information terminal is a portable information terminal.

In the blood pressure measurement system of one embodiment, the information terminal is a portable information terminal (for example, a smartphone). Since the portable information terminal is an information terminal possessed by the subject, the subject can reliably receive a notification that the sphygmomanometer should be set to the nighttime blood pressure measurement mode. Therefore, since the subject can reliably grasp that the sphygmomanometer should be set to the nighttime blood pressure measurement mode, the subject does not forget to set the sphygmomanometer to the nighttime blood pressure measurement mode.

As described above, according to the invention of the present application, it is possible to provide a blood pressure measurement system that includes a sphygmomanometer having a nighttime blood pressure measurement mode and can notify a subject that the sphygmomanometer should be set to the nighttime blood pressure measurement mode.

It is to be noted that the various embodiments described above can be appreciated individually within each embodiment, but the embodiments can be combined together. It is also to be noted that the various features in different embodiments can be appreciated individually by its own, but the features in different embodiments can be combined.

The invention claimed is:

1. A blood pressure measurement system comprising:
a sphygmomanometer having a nighttime blood pressure measurement mode for starting blood pressure measurement according to a schedule; and
an information terminal communicable with the sphygmomanometer, wherein
the sphygmomanometer comprises:
a first memory,
a first communication unit configured to perform communication with the information terminal,
a mode switch for inputting a mode setting instruction to set the sphygmomanometer to the nighttime blood pressure measurement mode, and
a first processor,
the information terminal comprises:
a second memory,
a second communication unit configured to perform communication with the sphygmomanometer,
an information terminal display, and
a second processor, and
the schedule is a type of schedule that defines, during nighttime, a plurality of blood pressure measurement start times at a predetermined time interval from an instruction time at which the mode setting instruction is input by the mode switch,
the first processor of the sphygmomanometer is configured to:
cause the first memory to store a dataset including a plurality of measurement times at which the blood pressure measurements were respectively performed during the nighttime in the nighttime blood pressure measurement mode, and
transmit the dataset to the information terminal through the first communication unit, and
the second processor of the information terminal is configured to:
receive the dataset from the sphygmomanometer through the second communication unit and store the dataset in the second memory,
act as a reminding time calculation unit to calculate:
the instruction time by subtracting the time interval from an earliest one of the plurality of measurement times during the nighttime based on the dataset stored in the second memory, and
a reminding time at which a subject is to be notified that the sphygmomanometer should be set to the nighttime blood pressure measurement mode based on the instruction time, and
act as a notification unit to notify the subject by causing reminder information indicating that the sphygmomanometer should be set to the nighttime blood pressure measurement mode to be displayed on the information terminal display at the reminding time, wherein
the first processor of the sphygmomanometer is further configured to:
when the mode setting instruction is input by the mode switch and the sphygmomanometer is set to the nighttime blood pressure measurement mode, determine, based on the instruction time, the plurality of blood pressure measurement start times at the predetermined time interval during the nighttime to thereby establish the schedule, and
perform control to start blood pressure measurement at each of the plurality of blood pressure measurement start times defined by the schedule.

2. The blood pressure measurement system according to claim 1, wherein
the dataset includes a date and a day of a week on which the blood pressure measurements were performed in the nighttime blood pressure measurement mode, and
the second processor of the information terminal is configured, when acting as the reminding time calculation unit, to:
calculate the instruction time for each date by subtracting the time interval from the earliest one of the plurality of measurement times for each respective date, based on the dataset stored in the second memory,
group the calculated instruction times by day of the week,
select a predetermined number of most recent instruction times for each day of the week, calculate an average instruction time for each day of the week from the selected instruction times, and
calculate the reminding time for each day of the week by subtracting a margin time from the average instruction time for that day of the week.

3. The blood pressure measurement system according to claim 1, wherein
the first processor of the sphygmomanometer is configured to transmit, through the first communication unit, a mode setting signal indicating that the mode setting instruction has been input when the mode setting instruction is input by the mode switch, and
the second processor of the information terminal is configured:
when acting as the reminding time calculation unit, to set, as the reminding time, an initial reminding time and one or more additional reminding times following the initial reminding time, and
when acting as the notification unit,
to perform notification by causing the reminder information to be displayed on the information terminal display when the initial reminding time arrives, and thereafter
to determine whether the mode setting signal has been received through the second communication unit, and
to repeat the notification at each of the additional reminding times when the mode setting signal has not been received, and to stop repeating the notification when the mode setting signal has been received.

4. The blood pressure measurement system according to claim 1, wherein
the first processor of the sphygmomanometer is configured to transmit the dataset to the information terminal through the first communication unit when blood pressure measurement is performed in the nighttime blood pressure measurement mode, and the second processor of the information terminal is configured, upon receiving the dataset from the sphygmomanometer through the second communication unit, to act as the reminding time calculation unit to calculate the reminding time.

5. The blood pressure measurement system according to claim 1, wherein the sphygmomanometer further comprises a communication switch for inputting a communication instruction enabling the communication between the sphygmomanometer and the information terminal, the first processor of the sphygmomanometer is configured, when the communication instruction is input by the communication switch, to transmit the dataset stored in the first memory to the information terminal through the first communication unit, and the second processor of the information terminal being configured, upon receiving the dataset from the sphygmomanometer through the second communication unit, to act as the reminding time calculation unit to calculate the reminding time.

6. The blood pressure measurement system according to claim 1, wherein the information terminal is a portable information terminal.

7. The blood pressure measurement system according to claim 1, wherein the sphygmomanometer comprises a first housing in which the first memory, the first communication unit, and the first processor are mounted, the mode switch being disposed on a surface of the first housing, the information terminal comprises a second housing in which the second memory, the second communication unit, and the second processor are mounted, the second housing being provided separately from the first housing, and the information terminal display being disposed on a surface of the second housing.

8. The blood pressure measurement system according to claim 1, wherein the sphygmomanometer comprises:

a band shaped blood pressure measurement cuff configured to be wrapped around a measurement site of the subject, a pump configured to supply air to the cuff, a valve configured to discharge air from the cuff, and a pressure sensor configured to detect pressure in the cuff, and the first processor of the sphygmomanometer is configured, upon starting each blood pressure measurement, to:

calculate the blood pressure of the subject by an oscillometric method based on an output of the pressure sensor during a pressurization process of the cuff in which air is supplied into an air bladder of the cuff by driving the pump, or during a depressurization process of the cuff in which the air is discharged from the air bladder of the cuff through the valve.

* * * * *